US011381643B2

(12) United States Patent
Feldhorst et al.

(10) Patent No.: US 11,381,643 B2
(45) Date of Patent: Jul. 5, 2022

(54) SYSTEM AND METHOD FOR MONITORING A WORK SITUATION

(71) Applicant: Fraunhofer-Gesellschaft zur Förderung der angewandten Forschung e.V., Munich (DE)

(72) Inventors: Sascha Feldhorst, Herne (DE); René Grzeszick, Dortmund (DE)

(73) Assignee: Fraunhofer-Gesellschaft zur Förderung der angewandten Forschung e.V., Munich (DE)

( * ) Notice: Subject to any disclaimer, the term of this patent is extended or adjusted under 35 U.S.C. 154(b) by 654 days.

(21) Appl. No.: 16/206,329

(22) Filed: Nov. 30, 2018

(65) Prior Publication Data

US 2019/0173953 A1 Jun. 6, 2019

(30) Foreign Application Priority Data

Dec. 4, 2017 (DE) ..................... 10 2017 221 852.5

(51) Int. Cl.
*H04L 67/12* (2022.01)
*G01D 21/02* (2006.01)
(Continued)

(52) U.S. Cl.
CPC ............. *H04L 67/12* (2013.01); *G01D 21/00* (2013.01); *G01D 21/02* (2013.01); *G06K 9/6262* (2013.01);
(Continued)

(58) Field of Classification Search
CPC .................................. H04L 67/12; H04W 4/38
See application file for complete search history.

(56) References Cited

U.S. PATENT DOCUMENTS 10,605,470 B1\* 3/2020 Saxena .................. G06V 20/52
2006/0000420 A1\* 1/2006 Martin Davies ..... A01K 29/005
119/174
(Continued)

FOREIGN PATENT DOCUMENTS

EP 1971055 A2 9/2008
EP 2720210 A1 4/2014
(Continued)

OTHER PUBLICATIONS

"European Application Serial No. 18 209 526.5, Office Action dated Oct. 20, 2020", (dated Oct. 20, 2020), 11 pgs.
(Continued)

*Primary Examiner* — Wen W Huang
(74) *Attorney, Agent, or Firm* — Schwegman Lundberg & Woessner, P.A.

(57) ABSTRACT

The application relates to a system for monitoring a working situation, said system comprising at least one mobile sensor unit, at least one communication node, at least one sensor node which is formed by the communication node or is provided additionally to this, and a central evaluation unit. The at least one mobile sensor unit comprises at least one sensor for measuring at least one first physical variable which is suitable for describing an activity or a state of an individual carrying the mobile sensor unit, a transmitter for the wireless transmission of measurement values of the at least one first physical variable, which are detected by the at least one sensor of this mobile sensor unit, to the at least one sensor node. The at least one sensor node comprises at least one sensor for measuring at least one second physical variable which is suitable for describing a state of an environment of the sensor node. The at least one communication node comprises a receiver for receiving the measurement values of the at least one first physical variable which are transmitted by the transmitter of the mobile sensor
(Continued)

Figure 1:
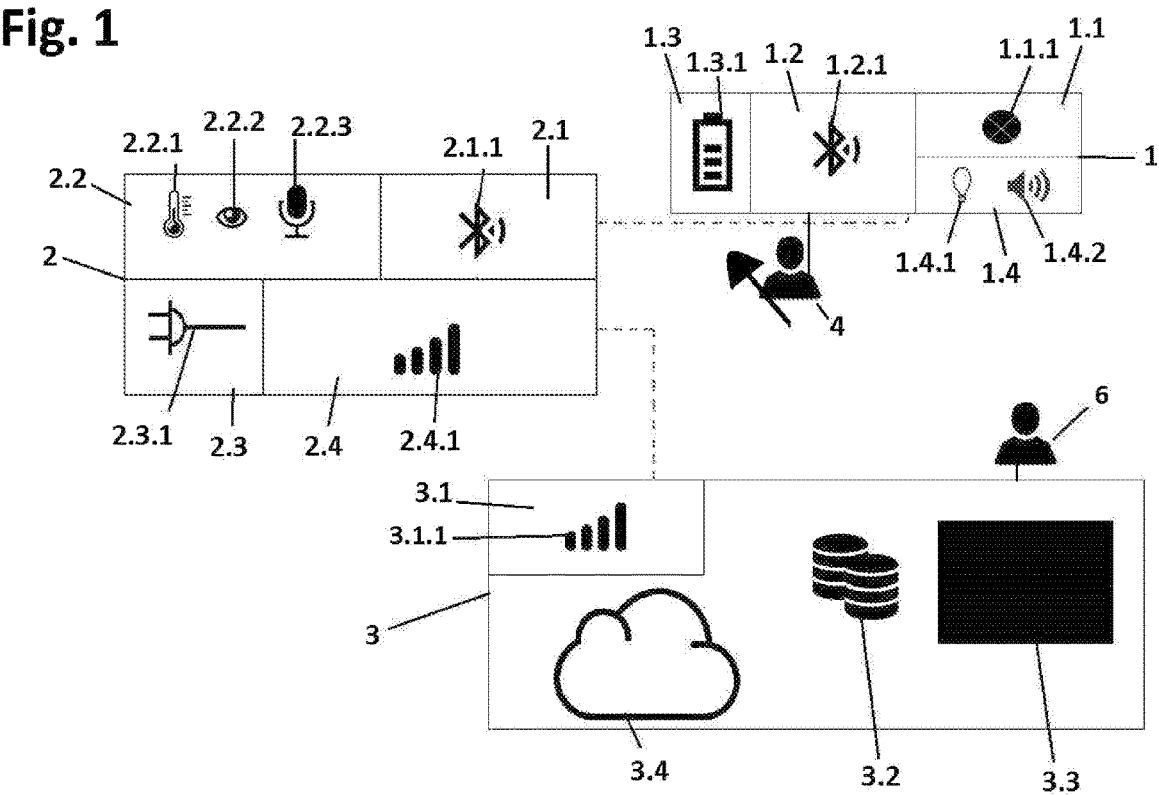

unit, and a communication unit for transmitting the measurement values of the at least one first physical variable which are received by the receiver of this communication node and measurement values of the at least one second physical variable, which are detected by the at least one sensor of the sensor node, to the central evaluation unit. The application further relates to a method for use of the system.

21 Claims, 4 Drawing Sheets

(51) Int. Cl.
    *G01D 21/00*     (2006.01)
    *G06Q 10/06*     (2012.01)
    *H04W 4/80*     (2018.01)
    *G06K 9/62*     (2022.01)
    *H04J 3/06*     (2006.01)
    *A61B 5/00*     (2006.01)

(52) U.S. Cl.
    CPC ........ *G06Q 10/0639* (2013.01); *H04J 3/0638* (2013.01); *H04W 4/80* (2018.02); *A61B 5/0004* (2013.01)

(56) References Cited

U.S. PATENT DOCUMENTS

| 2007/0159321 | A1 | 7/2007 | Tanaka et al. |
| 2015/0264091 | A1* | 9/2015 | Lin .......................... H04L 67/12 709/228 |
| 2016/0125348 | A1 | 5/2016 | Dyer et al. |
| 2016/0135109 | A1* | 5/2016 | Hampel .................. H04W 4/70 370/315 |
| 2016/0342906 | A1* | 11/2016 | Shaashua .............. H04W 4/029 |
| 2017/0278052 | A1 | 9/2017 | Brady |
| 2017/0280289 | A1* | 9/2017 | Skaaksrud ........ H04W 28/0252 |
| 2017/0312614 | A1* | 11/2017 | Tran .......................... A61B 5/11 |
| 2017/0318047 | A1* | 11/2017 | Hampel ................ H04W 8/005 |
| 2019/0183436 | A1* | 6/2019 | Yajima .................. A61B 5/002 |

FOREIGN PATENT DOCUMENTS

| EP | 3189310 A1 | 7/2017 |
| WO | WO-2017116802 A1 | 7/2017 |

OTHER PUBLICATIONS

"German Application Serial No. 10 22017 221 852.5, Examination Report dated Aug. 7, 2018", (dated Aug. 7, 2018), 7 pgs.

* cited by examiner

SYSTEM AND METHOD FOR MONITORING A WORK SITUATION

PRIORITY APPLICATIONS

This application claims the benefit of priority to German Application No. 10 2017 221 852.5, filed on Dec. 4, 2017, which is hereby incorporated herein by reference in its entirety.

The invention relates to a system for monitoring a working situation.

Different monitoring systems or monitoring methods for working processes are applied in the industrial field, for example in manufacturing and logistics. Some methods are based for example on video analyses, others on process observations by way of a present human observer. Still others acquire process-typical, physical variables of the working process via acceleration sensors.

Whereas methods which demand a human observer are particularly time-consuming and costly and the presence of the observer can moreover adulterate the measurements, methods with which no human observer is present have the disadvantage that an environment of the work and relevant contextual information are not registered. Furthermore, common methods demand a data evaluation which takes place after the gathering of data, on the basis of which evaluation processes can then be adapted in the future.

It is the object of the application to provide a system which allows for an automatic acquisition of working-process-relevant information as well as contextual information, the linking of both types of information with one another and the evaluation and processing of the data to be effected with sufficient speed to automatically analyse, improve and control process sequences for example in the industrial field, in particular in inner-operational logistics. Preferably, this would also render possible an advantageous adjustment of working processes during operation.

This is made possible by a system according to claim 1 of this application. Advantageous embodiments are to be derived from the dependent claims.

Such a system comprises at least one mobile sensor unit, at least one communication node, at least one sensor node which is formed by the communication node or is provided additionally thereto, and a central evaluation unit.

The at least one mobile sensor unit is envisaged to be carried or used by an individual carrying out a working process, and comprises at least one sensor for measuring at least one first physical variable which is suitable for describing an activity which is carried out by that individual or for describing a state of that individual. Herein, a mobile sensor unit is usually provided for each of several individuals, so that an individual is assigned to each mobile sensor unit. First physical variables in the context of the present document in particular are those physical variables which assume characteristic values on carrying out a certain working process and/or are suitable for recognising, analysing and/or assessing an execution of a working process. Amongst other things, the at least one mobile sensor unit can therefore serve for acquiring information which is relevant to the working process (working-process-relevant information).

The at least one mobile sensor unit further comprises a transmitter for the wireless transmission of measurement values of the at least one first physical variable detected by the at least one sensor of this mobile sensor unit to the at least one communication node.

Furthermore, the mobile sensor unit comprises an energy store for the electricity supply of the transmitter. In some embodiments, other components of the mobile sensor unit, such as for example the sensor, also require electricity and can likewise be supplied with electricity by the energy store.

The at least one sensor node comprises at least one sensor for detecting at least one second physical variable which is suitable for describing a state of the environment of the sensor node. Second physical variables in the context of this document are therefore variables which can describe a state of the environment of the respective sensor node. The at least one sensor node amongst other things can therefore serve for acquiring information on a working environment or on a working context of the respective individual who is present in the environment of the respective sensor node. The first physical variables and the second physical variables taken together then form the working situation of the respective individual.

The at least one communication node and the at least one mobile sensor unit are configured to communicate with one another in at least one direction. For this, the at least one communication node comprises a receiver, so that the first physical variables which are detected by the at least one sensor of the at least one mobile sensor unit can be transferred to the at least one communication node. The transmitter of the mobile sensor unit and the receiver of the communication node can be for example a Bluetooth transmitter and a Bluetooth receiver.

The at least one communication node further comprises a communication unit for transmitting the measurement values of the at least one first physical variable which are received by the receiver of this communication node and the measurement values of the at least one second physical variable, which are detected by the at least one sensor of the sensor node, to the central evaluation unit.

The central evaluation unit comprises a communication unit for receiving the measurement values of the at least one first physical variable and of the at least one second physical variable, said measurement values being transmitted by the communication unit of the sensor node.

The system is configured to assign the measurement values of the at least one second physical variable, which are detected by the at least one sensor of the sensor node to the mobile sensor unit, which is localised in the environment of this sensor node at least at one point in time, and to transfer these together with the measurement values of the at least one first physical variable, which are detected by the at least one sensor of the mobile sensor unit, which is localised in the environment of this sensor node at least at the point in time, to the central evaluation unit as being assigned to one another and there to store them and/or process them further. The first and second physical variables, which belong to the working situation of a single individual and which are measured at the same time and in the same environment, can therefore be assigned to one another. In particular, by way of this, one can determine which work was carried out and where.

Furthermore, the receiver of the at least one communication node can be suitable for localising the at least one mobile sensor unit. To this end it may, under certain circumstances, be sufficient for the receiver of the at least one sensor node to localise the mobile sensor unit or at least one of the mobile sensor units in an environment of the sensor node by way of a signal strength of a signal which is received from the transmitter of the mobile sensor unit exceeding a threshold. However, the localising can also be effected in another manner, for example by way of a bidirectional communication, as is described hereinafter, where in one embodiment, position data for the at least one mobile sensor unit can additionally be determined.

In embodiments of the described system, one avoids a pairing process having to take place in order to connect the mobile sensor unit to a communication node or sensor node. Instead, one can for example envisage making it possible for data to always be transmitted if the sensor unit is located in the proximity of a communication node or sensor node, for instance by way of continuous transmitting on the part of the mobile sensor unit and/or on the part of the sensor node.

The described system can be advantageously applied for example in the industrial field or in hospitals. It is particularly suitable for use in logistics, production or the field of nursing. Warehouse workers, production workers or medical personnel and/or care personnel etc. can then each be equipped with mobile sensor units.

One can also envisage an individual carrying more than one mobile sensor unit. Specifically, mobile sensor units for a single individual can be combined such that his/her activities can be acquired and assessed as comprehensively as possible.

An electricity supply of the at least one sensor node can be provided by way of battery or cell or via an electricity cable. A preferred embodiment of the electricity supply depends on the field of application, for example whether sockets are present in the proximity of the sensor node and whether the components on the sensor node which need to be supplied with electricity consume much electricity. Since the at least one sensor node does not usually need to be moved often, a battery or an accumulator of the at least one sensor node can be large and powerful.

In one embodiment, an anonymization of the measurement values can be envisaged. An assignment of the measured physical variables to specific individuals, of which each carries a mobile sensor unit, is rendered impossible in this embodiment, for example by way of the data which permit an assignment of the measured first or second physical variables to a certain mobile sensor unit being rejected or not being acquired at all. An anonymization can be desirable or advantageous for example to protect the privacy of the individual, for adhering to legal stipulations or in order to prevent an observer effect. For anonymization, one can also envisage the assignment of the data to the mobile sensor units continuing be possible, but information on the assignment of the mobile sensor unit to the individual not being acquired or being rejected.

In one embodiment, in which at least one communication node is sensor node, this at least one sensor node, which is also a sensor node, and the central evaluation unit are configured to assign the measurement values of the at least one second physical variable, which are detected by the at least one sensor of the sensor node, to the mobile sensor unit, which is localised in the environment of this sensor node by the receiver of this sensor node, and to store them and/or process them further together with the measurement values of the at least one first physical variable detected by the at least one sensor of the mobile sensor unit, which is localised in the environment of this sensor node, as being assigned to the mobile sensor unit.

The mobile sensor unit can be operated with a battery or with an accumulator. Processes on the mobile sensor unit are preferably reduced to that which is absolutely necessary in order to save weight and spare the battery or accumulator. For example, the processes which are carried out on the mobile sensor unit are restricted to the measurement and a forwarding of measurement values, whereas other steps which relate for example to the evaluation are preferably carried out on the central evaluation unit.

In order to measure the first physical variables, the at least one sensor of the at least one mobile sensor unit can be designed for example as an acceleration sensor, magnetometer or gyroscope or comprise an acceleration sensor and/or a magnetometer and/or a gyroscope. Thereby, in one embodiment, for example a speed or an acceleration of limbs can be measured on carrying out a certain movement, for example on handling a tool or carrying out an activity, by way of a suitable carrying or a suitable attachment to the body of an individual. This speed or acceleration then represents a first physical variable. Another example of a first physical variable is a position and a posture for example of limbs (extremities) or the spinal column of the individual. Furthermore, a temperature which is measured on the body, vital values, muscle activity or a pressure which acts upon a body part can also represent first physical variables, so that thermometers, a heart rate monitor, electrodes, for examine for electromyography (EMG), or pressure or position sensors are possible as sensors of the mobile sensor unit. The first physical variables can serve for example for identifying an activity or for monitoring the correct execution of the activity, in order for example to identify an incorrect execution which is harmful to health. The at least one mobile sensor unit can comprise a single sensor or several different sensors. The mobile sensor units can be designed equally or differently in the case of a system with several mobile sensor units.

The at least one sensor of the at least one sensor node can, amongst other things, be for example a temperature sensor, a brightness sensor, a vibration sensor, an acoustic sensor for measuring the noise level of an environment, a radiation detection device, a Geiger counter, a dosimeter, a barometer, a hygrometer or a sensor for measuring a gas content, for example an oxygen content, carbon monoxide content or carbon dioxide content, of the surrounding air or comprise one or more of these sensors.

One advantage of the suggested system lies in the fact that an equipping of the mobile sensor unit can be limited to those sensors which demand an essentially direct contact to the individual carrying the mobile sensor unit in order to permit the measurement of variables which describe his state or his activity. In contrast, other functions can advantageously be outsourced to the sensor nodes. The mobile sensor unit can therefore be designed in a particularly small and lightweight manner. The suggested system thus allows for the a much more comprehensive measurement of a working situation of the respective individual than would be possible using only the comparatively small, lightweight and simply designed mobile sensor unit. One benefit lies in the individual not being inhibited in carrying out his activity and furthermore no psychological observer effect occurring. In some embodiments, this can be further assisted by way of the mobile sensor unit being designed as a wearable, thus as a unit which is portable on the body, for example in the form of clothing or the like or being integrated into such a wearable. The mobile sensor unit can be designed for example as a glove or as an armband or be integrated into a glove or an armband. It can be suitable for carrying in a pocket or for example be integrated into clothing in order to monitor a body posture. The mobile sensor unit can also be integrated into a tool or into a vehicle, for example into a fork-lift truck. The design and the fashion of the wearable can be dependent for example on the type of sensors and the activity which is to be monitored. A mobile telephone of an individual can also be used as a mobile unit for some applications.

Several such wearables can also be combined for a single individual in order to acquire his movements and activities in as comprehensive a manner as possible. The several wearables of the one individual can each represent an individual mobile sensor unit. The several wearables of an individual however can also belong to the same mobile sensor unit and each comprise sensors which belong to this mobile sensor unit.

In an embodiment, the at least one mobile sensor unit can comprise a receiving unit and the at least one sensor node a transmitting unit. A bidirectional wireless communication between the at least one mobile sensor unit and the at least one sensor node can be made possible by way of this, in order for example to send feedback to the individual or individuals who carry the at least one mobile sensor unit. By way of this, it is likewise rendered possible to transmit measurement values which are detected by the sensor node to the mobile sensor unit, so that they can be transmitted from there to a communication node, should the sensor itself not be a communication node. The bidirectional wireless communication can be effected for example via Bluetooth. The transmitting unit of the at least one sensor node can further be used as a radio beacon, by way of a beacon signal being sent for localising the at least one mobile sensor unit. On localising by way of a radio beacon, detailed position data for the at least one mobile sensor unit may also be gathered, stored and evaluated together with the first and second physical variables and assigned to these.

The at least one mobile sensor unit can be configured to detect if it is localised in the environment of a sensor node by way of signals of this sensor node, which are received by its receiving unit, said sensor node acting as a radio beacon.

With regard to the described system, the mobile sensor unit can be configured to receive measured values of the at least one second physical variable, which are detected by the at least one sensor of the at least one sensor node, with its receiving unit, if it is localised in the environment of this sensor node. The mobile sensor unit is then further configured to transmit these received measurement values together with the measurement values of the at least one first physical variable, which are detected by its at least one sensor, to the receiver of the communication node if or as soon as the communication node is in reach of its transmitter.

Furthermore, the at least one mobile sensor unit can comprise a memory. This is configured to intermediately store the measurement values of the at least one second physical variable, which are detected by the at least one sensor of the at least one sensor node, and are received by the mobile sensor unit with its receiving unit. Furthermore, it is configured to intermediately store the measurement values of the at least one second physical variable, which are detected by the at least one sensor of the mobile sensor unit itself. The intermediate storage of the different measured values is herein effected in a time-resolved and in a temporally assigned manner.

One can envisage the mobile sensor unit and the communication node each comprising a clock and being configured to synchronise these clocks. This makes it possible to compensate a possible drift of the clock of the mobile sensor unit. It has been found that a drift of the clock of the mobile sensor unit can noticeably influence the accuracy of the system. The communication nodes can be supplied with energy, for example via an electricity grid, and comprise more accurate clocks than the mobile sensor units. Timestamps of the measurement values of the first and second physical variables which are intermediately stored in the memory of the mobile sensor unit and which are present there as measurement value pairs, which are time-resolved and assigned to one another, can be corrected by way of a comparison of the clock of the mobile sensor unit with the clock of the communication node. For example, the clock of the mobile sensor unit can be synchronised with the communication node at the beginning of the measurement. After completion of the measurement, if the mobile sensor unit has been brought back to the communication node for the transmission of the measurement values which are intermediately stored on it, a possible drift of the clock of the mobile sensor unit vis-à-vis the clock of the communication node can be ascertained and corrected for example. For example, a linear adaptation of the timestamp can be carried out.

In an embodiment, the communication unit of the at least one communication node and the complementary communication unit of the central evaluation unit are designed for the bidirectional communication between the at least one communication node and the central evaluation unit. The feedback can thus be transmitted from the central evaluation unit via the at least one communication node to the at least one mobile sensor unit.

The communication unit of the at least one communication node and the communication unit of the central evaluation unit can either be designed as wireless communication units or as communication units which demand a cable. All connections with an adequate transmission rate are considered as a connection between the communication units. The transmission can be effected for example via a local network (LAN), a wireless local network (WLAN), a low power wide area network, such as for example NarrowBand IoT (NB-IoT) or via a mobile communications network, for example 3G, 4G or 5G. Different embodiments can be preferred depending on the application and the location of application, for example depending on whether a LAN or WLAN infrastructure is available at the location of application.

In one embodiment, in order to provide the feedback, the at least one mobile sensor unit can comprise a feedback device for transferring information to the respective individual carrying the mobile sensor unit. This information can comprise for example warnings or instructions. For example, the feedback device can be designed to send the mentioned information as an optical signal, as a sound signal, via a display, as a haptic feedback or as a vibration to the respective individual carrying the mobile sensor unit. The individual can therefore be instructed by a feedback signal, for example to take a break, correct his posture or to leave the room in which he is presently located. It is also possible to set the individual a task via the feedback function, for example the individual can be requested to assume another task at another location.

The information or instructions or warnings which are sent to the individual via the feedback function can be based on the measurement values of the first and second physical variables, which are processed by way of the central evaluation unit, or on the results of this evaluation.

However, the feedback can also be sent to the individual without a communication having had to take place with the central evaluation unit. For example, the transmission can also take place based on measurement values of the first physical variable, which are detected by the sensors of the mobile sensor unit itself and/or on the basis of the measurement values of the second physical variable, which are transferred to the mobile sensor unit.

One can envisage the at least one communication node being configured for localising the mobile sensor unit.

In a system, with regard to which the at least one communication node forms a sensor node, the at least one communication node and the central evaluation unit can be configured to assign the measurement values of the at least one second physical variable, which are detected by the at least one sensor of the sensor node which is formed by this communication node, to the mobile sensor unit which is localised in the environment of this communication node by the receiver of this communication node and to store them and/or further process them together with the measurement values of the at least one first physical variable, which are detected by the at least one sensor of the mobile sensor unit, which is localised in the environment of this communication node, as being assigned to one another.

The result may be a system for monitoring a working situation according to this application, said system comprising at least one mobile sensor unit, at least one sensor node and a central evaluation unit, wherein the at least one mobile sensor unit comprises at least one sensor for measuring at least one first physical variable which is suitable for describing an activity or a state of an individual carrying the mobile sensor unit, a transmitter for the wireless transmission of measurement values of the at least one first physical variable, which are detected by the at least one sensor of this mobile sensor unit, to the at least one sensor node, and an energy store for the supply of electricity to the transmitter, wherein the at least one sensor node comprises a receiver for receiving the measurement values of the at least one first physical variable, which are transmitted by the transmitter of the mobile sensor unit, and for localising the mobile sensor unit, at least one sensor for measuring at least one second physical variable, said variable being suitable for describing a state of an environment of the sensor node, and a communication unit for transmitting the measurement values of the at least one first physical variable, which are received by the receiver of this sensor node, and measurement values of the at least one second physical variable, which are detected by the at least one sensor of this sensor node, to the central evaluation unit and wherein the central evaluation unit comprises a communication unit for receiving the measurement values of the at least one first physical variable and of the at least one second physical variable, said measurement values being transmitted by the communication unit of the sensor node, wherein the at least one sensor node and the central evaluation unit are configured to assign the measurement values of the at least one second physical variable, which are detected by the at least one sensor of the sensor node to the mobile sensor unit, which is localised in the environment of this sensor node by the receiver of this sensor node, and to store them and/or further process them together with the measurement values of the at least one first physical variable, which are detected by the at least one sensor of the mobile sensor unit, which is localised in the environment of this sensor node, as being assigned to one another.

The system can be designed to carry out the transmission of measurement values of the at least one first physical variable and possibly measurement values of the at least one second physical variable from the at least one mobile sensor unit onto the at least one communication unit and the transmission of the measurement values of the at least one first and of the at least one second physical variable from the at least one communication node onto the central evaluation unit as well as a processing of the measurement values of the at least one first and of the at least one second physical variable by way of the central evaluation unit within at the most a few seconds. Preferably, all mentioned steps are effected in real time, thus only with a minimal, unavoidable delay. The most modern of transmission techniques as well as high-power computers and high-performance algorithms are applied for this.

The central evaluation unit can be suitable for example for reproducing, for evaluating and/or for storing information.

In an embodiment, the readings of the first and second physical variables are compared to predefined threshold values on the central evaluation unit.

In an embodiment, the measurement values of the first and/or second physical variables are evaluated on the central evaluation unit by way of algorithms of machine learning and/or pattern recognition. In an embodiment, heuristic methods are used for evaluating the readings.

In an embodiment, the central evaluation unit comprises or uses a cloud infrastructure.

In an embodiment, a continuous comparison of the determined first and second physical variables of a working context of each individual with threshold values is effected on the central evaluation unit or on the mobile sensor unit, so that on exceeding one of the threshold values, a corresponding feedback to the respective individual can be effected essentially immediately.

The central evaluation unit can comprise an operator interface. For example, output and input devices such as a screen or keyboard can be provided in order to give the operator the possibility of monitoring the system, keeping the data in view and/or intervening in the system. For example, a possibility is given to the operator of initiating an assignment of tasks or of sending other information to the respective individual carrying the at least one mobile unit via the at least one mobile unit, by way of intervening in the system.

The construction of the system which is described here permits a simple exchange of the sensor nodes or communication nodes and of the mobile sensor units, for example for servicing or renewing the nodes or units or for charging a battery of the nodes or units.

In systems with several mobile sensor units and/or sensor nodes, the mobile sensor units or sensor nodes can be designed equally or differently.

In one embodiment, different sensor nodes can be provided with different sensors.

In an embodiment, different mobile sensor units are equipped with different sensors and/or a feedback function.

In an embodiment, the at least one mobile sensor unit can be designed to record data of the sensor of the at least one mobile sensor unit and to transfer it to a communication node at a later point in time. Thus for example work or movements which are not carried out in the proximity of a communication node can be recorded. In one embodiment, position data, for example beacon signals which are received by the mobile sensor unit, WLAN signals from routers which are located in the environment or GPS data can be recorded and transferred to a communication node at a later point in time. In one embodiment, apart from the communication node, additional radio beacons, which are not communication nodes or sensor units, are provided for this. In one embodiment, the mobile sensor unit comprises a GPS receiver.

In one embodiment, more mobile sensor units than sensor nodes are provided.

The application also relates to a method for use of the described system. All features which have been described in the context of the system can be used in such a method.

A system according to the application can be used for example for process analyses or for the process control on working sites, such as for example in production, in logistics or in hospitals.

The sensor nodes are provided at locations of working sites, in particular the working sites' trouble spots or at points of the working sites particularly relevant to safety, for example in aisles or in a commissioning base, or for example in particularly cold or warm environments.

If they are not formed by the sensor nodes, the communication nodes can be arranged at locations of the working sites which the individuals regularly pass by. However, they can also be provided for example in changing rooms, at an entrance or in an office.

One or more individuals who undertake activities at the workplaces or working sites can each carry a mobile sensor unit.

Such a system or such a method allows for an improvement and acceleration of inner-operational sequences as well as an increase in work safety and an improvement of ergonomics.

Exemplary embodiments are shown in the figures.

Figure 2:
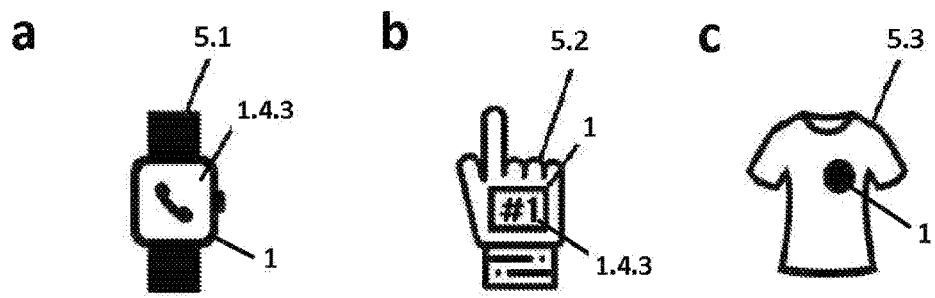
Figure 3:
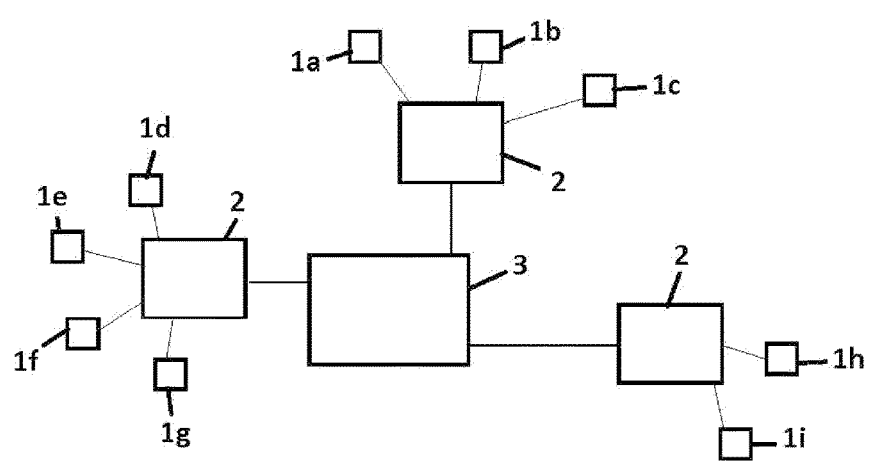
Figure 4:
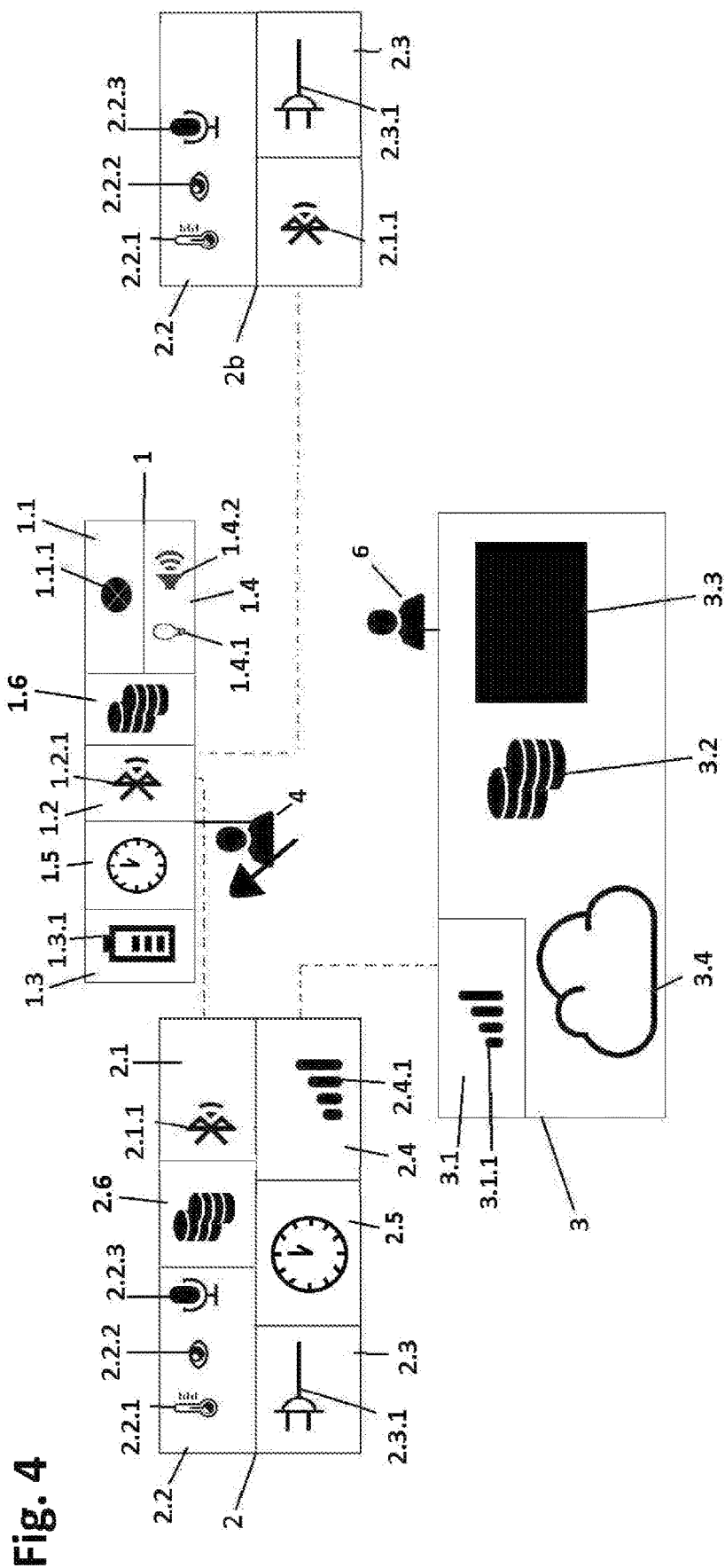
Figure 5:
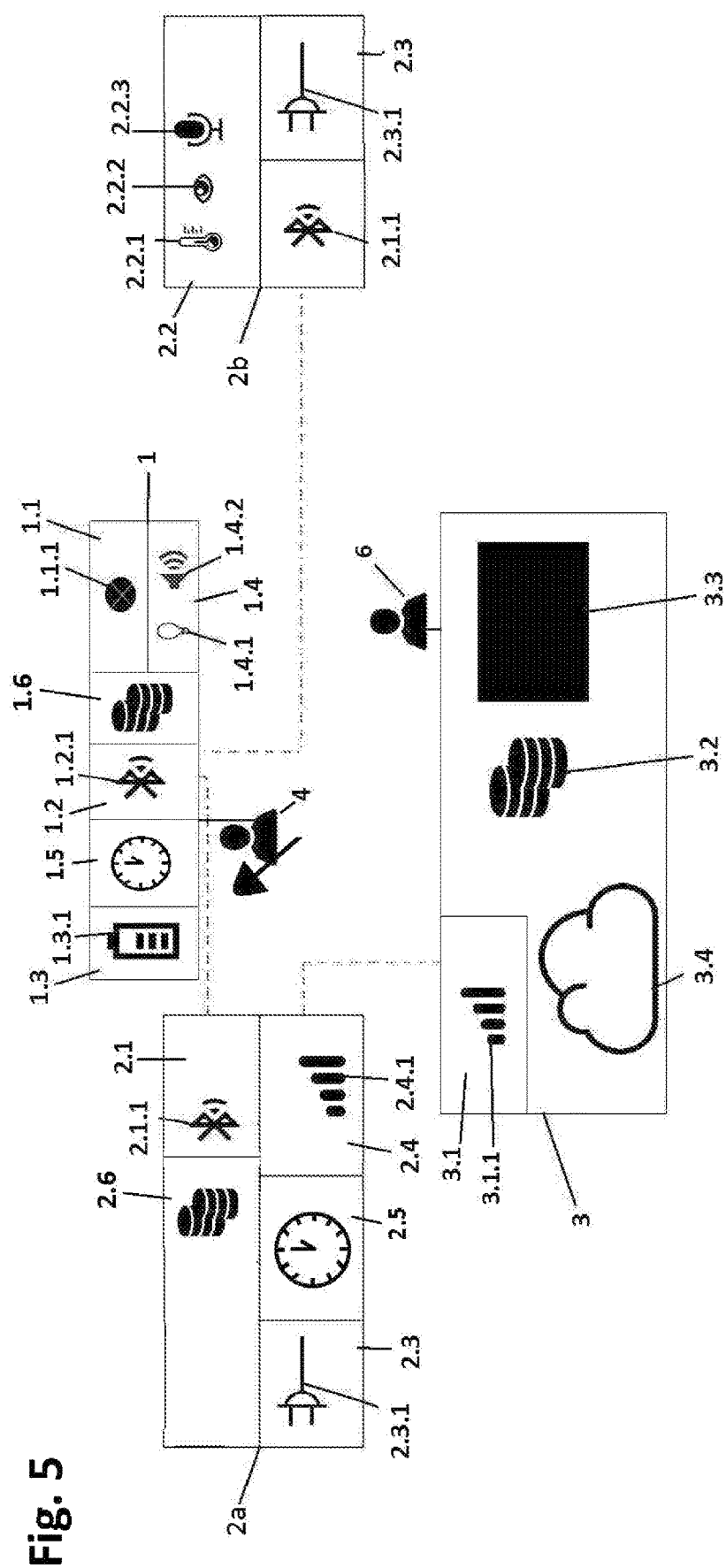

FIG. 1 schematically shows a system for monitoring a working situation with a mobile sensor unit, with a sensor node which is designed as a communication node, and a central evaluation unit with its respective components;

FIG. 2 schematically shows various wearables, each with integrated mobile sensor units of the type of mobile sensor unit from FIG. 1;

FIG. 3 schematically shows a system for monitoring a working situation with several mobile sensor units, several sensor nodes which are designed as communication modes, and with a central evaluation unit, with regard to which it is an extension of the system of FIG. 1;

FIG. 4 schematically shows a first variation of the system of FIG. 1;

FIG. 5 schematically shows a second variation of the system of FIG. 1 and

Figure 6:
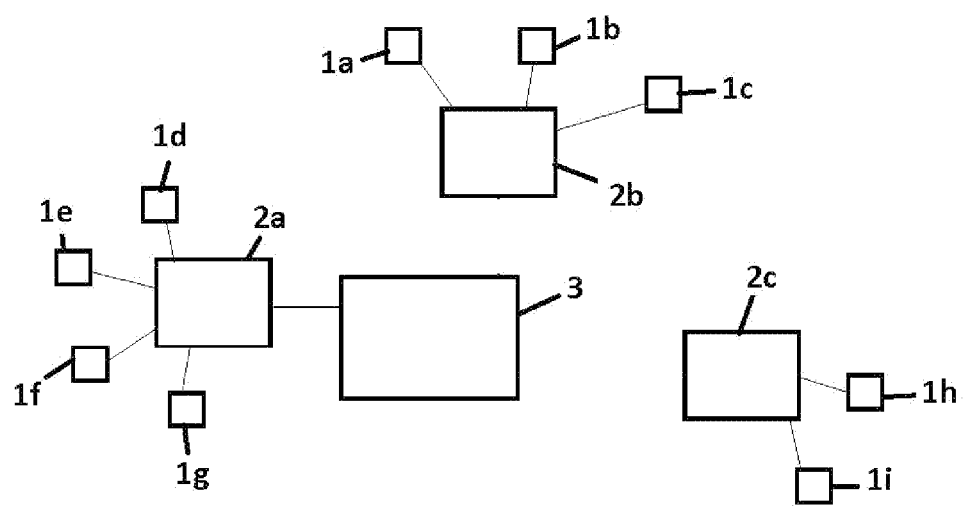

FIG. 6 schematically shows a system for monitoring a working situation with several mobile sensor units, several sensor nodes, a communication node and a central evaluation unit, with regard to which it is an extension of the system of FIG. 4 or 5.

FIG. 1 shows an example of a system according to the invention. A mobile sensor unit 1, a sensor node 2 and a central evaluation unit 3 are represented by way of example.

Using the system, the mobile sensor unit is worn by an individual 4 on carrying out a manual activity or on carrying out different manual activities or on carrying out working processes. The mobile sensor unit 1 comprises one or more sensors 1.1. The at least one sensor 1.1 serves for detecting one or more first physical variables which describes or describe a state of the individual 4 during these activities or processes. The at least one first physical variable serves for identifying whether the individual 4 is presently carrying out a certain activity or a certain process. For this, the at least one sensor 1.1 can be an acceleration sensor 1.1.1, a magnetometer or a gyroscope or comprise an acceleration sensor and/or a magnetometer and/or a gyroscope. The mobile sensor unit comprises a transmitting unit or a transmitting and receiving unit 1.2. The transmitting unit or the transmitting and receiving unit 1.2 comprises a Bluetooth antenna 1.2.1, however it can additionally or alternatively comprise another antenna, for example a WLAN antenna.

The transmitting unit or the transmitting and receiving unit 1.2 is preferably designed such that it consumes as little electricity as possible. The mobile sensor unit 1 comprises an energy supply 1.3, preferably comprising a battery or accumulator 1.3.1. Components of the mobile sensor unit 1 which require electricity are supplied via the energy supply. For example, the energy supply is designed for the use of an exchangeable battery or an exchangeable accumulator, which can be quickly exchanged during a use of the system, so that the mobile sensor unit is available at all times and does not need to be connected to a charging station for charging.

The mobile sensor unit further comprises a feedback function 1.4. The feedback function 1.4 comprises one or more units for sending a signal to the individual 4. Thus for example it can comprise a feedback lamplet 1.4.1 and/or a feedback loudspeaker 1.4.2 in order to send simple flashing or sound signals to the individual. However, it can also comprise other types of feedback functions, for example a vibration unit for sending a haptic feedback, or a display.

In addition or as an alternative to the components shown in FIG. 1, the mobile sensor unit can comprise further components, for example additional sensors other than the acceleration sensor 1.1.1. Components, for example the feedback function 1.4, can also be omitted. The precise design of the sensors 1.1, of the energy supply 1.3, of the communication unit 1.2 and of the feedback function 1.4 can be derived by the person skilled in the art depending on which types of processes are to be analysed and whether processes are to be controlled in a continuous manner.

The sensor node 2 comprises a receiving unit or transmitting and receiving unit 2.1. The receiving unit or transmitting and receiving unit 2.1 is designed for communication with the transmitting unit or transmitting and receiving unit 1.2 of the mobile sensor unit 1 and can accordingly likewise comprise a Bluetooth antenna 2.1.1 and/or another antenna. The receiving unit or transmitting and receiving unit 2.1 can be configured for use as a radio beacon for a localisation of the mobile sensor unit 1 or several mobile units, in order to acquire position data of the mobile sensor unit 1 or of several mobile units. The receiving unit or the transmitting and receiving unit 2.1 is further configured for receiving the one or more first physical variables which are detected by the sensor 1.1 and which are sent via the transmitting unit or transmitting and receiving unit 1.2 of the mobile sensor unit 1. The communication between the mobile sensor unit 1 and the sensor node 2 is indicated in the figure by a dashed line.

The sensor node 2 comprises one or more sensors 2.2 for measuring one or more second physical variables. For example, the at least one sensor 2.2 can be a temperature sensor 2.2.1, a brightness sensor 2.2.2 or a sound sensor 2.2.3 or comprise one or more of these. Yet further sensors can be present amongst the sensors 2.2, such as for example a radiation detection device, a sensor for measuring vibrations or air pressure, or sensors for example for measuring an oxygen content or carbon monoxide content or carbon dioxide content of the surrounding air. These second physical variables describe an environment of the sensor node, in which the manual activity is carried out by the individual 4 carrying the mobile sensor unit 1 which is in communication with the sensor node 2. Herein, the second physical variables do not need to be measured directly at the mobile sensor unit, since they can be constant or roughly constant for example in an entire space representing the environment in which the manual activity is carried out. This may, for example, apply to a temperature, a brightness, a radiation contamination level, a gas concentration or a sound volume. For example, the environment can be a cooling room/space or a direct vicinity of a furnace or of a radiation source or of an exhaust gas source, i.e. it may feature low or high temperatures or a radioactive radiation or air contamination which could harm the individual if he stays there too long, especially while carrying out activities. These second physical variables do not need to be measured on the mobile sensor unit 1. For the analysis of the working situation of the individual carrying the mobile sensor unit 1, it is sufficient to measure the second physical variables at the sensor node and then carry out the localisation of the mobile sensor unit 1. Processes which are carried out on the mobile sensor unit can therefore be minimised, or measurement devices which are too large to be worn by the individual 4 or which consume too much electricity in order to be fed by the energy supply 1.3 of the mobile sensor unit 1 can be provided. This also allows for a cost reduction of the mobile sensor unit 2. This is particularly preferred if significantly more mobile sensor units 1 than sensor nodes 2 are part of the system.

The system is configured to recognise, for example, a situation which is dangerous for the individual, based on certain thresholds being exceeded. If for example, as described above, the environment is a cooling space or the direct vicinity of a furnace, then after a predefined time, the system can send a warning via the feedback function 1.4 to the individual 4 present there or carrying out activities there, or prompt him to leave the environment or surroundings.

Different sensors 2.2 can be useful in different environments of different sensor nodes 2. A restriction to these sensors which are necessary in the respective environment can be effected in each environment due to the arrangement of the sensors for the second physical variables at the sensor node. Furthermore, costs can be saved by way of a centralisation of the measurement of second physical variables at the sensor nodes 2. The sensor node 2 comprises an energy supply 2.3. The energy supply 2.3 can comprises a mains plug 2.3.1 in order to keep the sensor node 2 as service-free as possible and to render unnecessary any exchange of batteries or accumulators. The sensor node 2 can however also be operated with a battery or with an accumulator instead of this, in order to render additional infrastructure such as an electricity mains unnecessary.

The sensor node 2 is simultaneously designed as a communication node. This means that it further comprises a communication unit 2.4 for communication with the central evaluation unit 3. The communication unit 2.4 is preferably designed as a wireless communication unit and comprises for example an antenna 2.4.1 for the use of a mobile communications network or another wireless network. For example, current high-speed mobile radio standards are used for communication, for example 3G or LTE or 4G or 5G, or a low power wide area network (LPWAN) such as for example NarrowBand IoT (NBIoT). However, the communication unit 2.4 can also be designed for WLAN communication or a connection with cables.

The central evaluation unit 3 comprises a communication unit 3.1 for communication with the communication unit 2.4 of the sensor node 2. Accordingly, the communication unit 3.1 of the central evaluation unit 3 is designed as the communication unit 2.4 of the sensor node 2, for example as a wireless communication unit, comprising for example a mobile radio antenna 3.1.1, or in another embodiment designed for a connection by cable. The communication between the central evaluation unit 3 and the sensor node 2 is indicated in the figure by a dashed line.

The central evaluation unit 3 is designed for storing and processing or evaluating data which is transferred from the sensor node 2 and from the at least one mobile sensor unit 1 to the central evaluation unit via the sensor node 2. This data comprises the first and second physical variables and in some embodiments can also comprise position data. For this, the central evaluation unit comprises or uses a data bank 3.2, in which raw data of the first and second physical variables, position data and evaluation results can be stored. The first and second physical variables are preferably stored in an assigned manner, so that first physical variables, which are transferred from a certain mobile sensor unit 1 to a certain sensor node 2 and are forwarded from this certain sensor node to the central evaluation unit 3, are assigned to the second physical variables which are simultaneously detected by the certain sensor node 2. The measurement values of the first physical variables which are transferred to the central evaluation unit 3 are assigned to a certain activity with the help of algorithms of machine learning, for identification of a certain working process. The identified working process is linked with the second physical variable. In this way, the working situation of the individual 4 carrying this certain mobile sensor unit, said situation encompassing a state of the individual 4 and a state of the environment of the individual 4, is identifiable as such at a certain point in time of the measurement. Furthermore, a position of the individual 4 is also detected by way of the assignment of its certain mobile sensor unit 1 to the certain sensor node 2 at the certain point in time of the measurement, or in some embodiments also by way of the position data which is gathered in parallel. The data of several mobile sensor units can be statistically evaluated for the analysis of the processes. For evaluating and the further processing of the data from the data bank 3.2, the central evaluation unit can use cloud technology 3.4 for optimising the evaluation of the data, in particular with large data quantities or with high and/or fluctuating required capacities.

Furthermore, the central evaluation unit 3 can comprise a user interface 3.3 by way of which data can be displayed to an operator 6 of the system and/or by way of which the operator 6 can intervene in the system 6. To this end, the operator interface 3.3 can comprise for example output devices, for example a screen for displaying a user interface and input devices, such as for example a keyboard and mouse.

FIGS. 2*a-c* show different wearables 5.1, 5.2, 5.3, into each of which a mobile sensor unit 1 is integrated. Each integrated mobile sensor unit 1 is constructed as is shown for example in FIG. 1 or similarly to that in FIG. 1 and can comprise all or a part of the components of the mobile sensor unit 1 which is shown in FIG. 1. For example, the feedback function 1.4 or one of the possible embodiments of the feedback functions 1.4.1, 1.4.2 can be omitted or designed differently. The mobile sensor unit can also comprise further components which are not shown in FIG. 1, for example additional sensors apart from the acceleration sensor 1.1.1, additionally to or instead of the components of the mobile sensor unit 1 shown in FIG. 1. Depending on which type of process is to be analysed, it is obvious to the person skilled in the art which type of wearable the mobile sensor unit 1 is advantageously integrated, which sensors are used and how the sensors, the energy supply 1.3, the communication unit 1.2, and the feedback function 1.4 of the mobile sensor unit 1 are advantageously designed.

FIG. 2*a* shows an armband 5.1 or a wearable similar to a wrist watch, into which a mobile sensor unit 1 is installed. The mobile sensor unit 1 in the shown example comprises the feedback function 1.4 which comprises a feedback display 1.4.3, via which communications such as for example warnings and instructions can be displayed to the individual 4. The mobile sensor unit 1, which is installed into the armband 5.1, further comprises for example a sensor 1.1, which is designed as an acceleration sensor 1.1.1 and which is designed to detect arm movements of the individual.

FIG. 2b shows a wearable which is designed as a glove 5.2 and into which the mobile sensor unit 1 is integrated. The mobile sensor unit 1 comprises for example a sensor 1.1, which comprises an acceleration sensor 1.1.1 and a sensor for detecting a finger position of glove fingers, with which sensor one can ascertain for example whether a hand of the individual 4 wearing the glove 5.2 is open or closed. Furthermore, in the shown example, a feedback display 1.4.3 is arranged for example on the back of the glove 5.2

FIG. 2c shows a wearable which is designed as a T-shirt 5.3, with an integrated mobile unit 1. If it is integrated into a T-shirt, the mobile sensor unit 1 can comprise for example sensors 1.4, with which a position of an upper body or spinal column position of the individual 4 can be detected.

FIG. 3 shows a system according to the application, with several mobile sensor units 1a-i and several sensor nodes 2 which are each designed as communication nodes. Each of the mobile sensor units 1a-i and each of the sensor nodes 2 is herein designed as or similarly to the mobile sensor units 1 and the sensor nodes 2 of FIGS. 1 and 2. The precise embodiment of the individual mobile sensor units 1a-i and of the individual sensor nodes 2 can herein be equal or different. The number of the mobile sensor units 1a-i and of the sensor nodes 2 is selected in the figure by way of example. An arbitrary number of sensor nodes 2 and an arbitrary number of mobile sensor units 1 can belong to the system. Herein, as is indicated in FIG. 3 by the lines, the sensor nodes 2 as communication nodes can be in communication with the central evaluation unit 3, for example by way of a mobile communications network, a 3G, 4G or 5G connection, via a low power wide area network (LPWAN), such as for example NarrowBand lot (NB-IoT), or via a local network which can be designed in a wireless manner, for example as WLAN, or be designed with cable connections. The mobile sensor units 1a-i are each in communication with one of the sensor nodes 2, for example via a Bluetooth connection. Each of the sensor nodes 2 can be used for example as a radio beacon and sends a beacon signal, by which means a localisation of the mobile sensor units in the proximity of the respective sensor node 2 is made possible. Each of the mobile sensor units 1a-i can be assigned to one of the sensor nodes 2 on the basis of a position of each mobile sensor unit 1a-i and connect to this in a wireless manner and create for example a bidirectional data connection. As is indicted by lines, the mobile sensor units 1a-c are assigned to the sensor node 2b, the mobile sensor units 1d-1g to the sensor node 2c and the mobile sensor units 1i-h to the sensor node 2c. This assignment can be effected for example due to fact that the mobile sensor units 1a-i are each located in the same room as the respectively assigned sensor node 2, or due to the mobile sensor units 1a-i have a certain maximum distance to the respectively assigned sensor node 2. If one of the mobile sensor units 1a-i moves away from the respectively assigned sensor node 2 towards another of the sensor nodes 2, then this one of the mobile sensor units 1a-i can be assigned to the other of the sensor nodes 2.

FIG. 4 shows a system for monitoring a working situation, which, as with the system which is represented in FIG. 1, comprises a mobile sensor unit 1, a central evaluation unit 3 and a sensor node 2, wherein the sensor node 2 is simultaneously a communication node.

In addition, the system comprises a further sensor node 2b, which is not designed as a communication node. The sensor node 2b is supplied with electricity via the electricity mains and as sensors 2.2 has at its disposal a temperature sensor 2.2.1, a brightness sensor 2.2.2 and a sound sensor 2.2.3. The further sensor node 2b moreover has at its disposal a Bluetooth antenna 2.1.1, which is configured as a transmitting unit and constantly emits a signal which comprises the measured values detected by its sensors 2.2 at that respective point in time, i.e. the respective latest measurement values of the second physical variables.

If the mobile sensor unit 1 is located within the range of the further sensor node 2b, then the mobile sensor unit receives the signal 1 via its Bluetooth antenna 1.2.1 containing the measurement values which are emitted by the second sensor node 2b. Apart from the measurement values, information which permits an identification of the further node 2b can also be contained in the emitted signals.

The measurement values which are received by mobile sensor unit 1 in this manner are intermediately stored in a memory 1.6 of the mobile sensor unit 1. At the same time, measurement values of one or more first physical variables are determined by the sensor 1.1 of the mobile sensor unit itself and are likewise intermediately stored. The storage is effected in a manner assigned in pairs, so that measurement values of the first and second variables, which have been simultaneously gathered, can be assigned to one another. Measurement value pairs which are generated in this manner are therefore suitable for describing in a time-resolved manner the working situation of the individual 4 carrying the mobile sensor unit. The stored measurement value pairs are provided with a timestamp so that one can conclude when this working situation was present. For this, the mobile sensor unit has a clock 1.5. The possible data for the identification of the further node 2b can likewise be intermediately stored on the mobile sensor unit so that one can deduce the sensor node in whose environment the measurement values of a specific measurement value pair have been gathered.

The sensor node 2, which is likewise present in the system and which is simultaneously designed as a communication node, has essentially the same functionality as the sensor node which is described in the context of FIG. 1. Furthermore, it is however also configured to receive the data which is intermediately stored in the memory 1.6 of the mobile sensor unit 1, i.e. the measurement value pairs with the timestamp, if the mobile sensor unit is located within the reach of its transmitting and receiving unit 2.1. The sensor node 2 likewise comprises a clock 2.5. One envisages this clock 2.5 being compared with the clock 1.5 of the mobile sensor unit 1. Herein, the clock 1.5 of the mobile sensor unit 1 can be synchronised with the clock 2.5 of the sensor node 2 if a communication connection exists. If after a disconnection and a later renewed creation of the communication connection it is ascertained that the clock 1.5 of the mobile sensor unit 1 has, in the meantime, deviated from the clock of the sensor node 2, then the timestamps of the measurement value pairs which are intermediately stored on the mobile sensor unit 1 can be corrected. The measurement values which are received from the sensor and communication node 2 are likewise transferred to the central evaluation unit. Likewise, the measurement values of the second physical variables which are gathered on the sensor and communication node 2 are transferred to the central evaluation unit, together with the measurement values of the first physical variables which are gathered on the mobile sensor unit 1 whilst this is located in its environment.

FIG. 5 shows a system which differs from the system of FIG. 4 in that the communication node 2*a* is not simultaneously a sensor node. In this case the purpose of the communication node 2*a* is therefore to receive the measurement value pairs which were previously intermediately stored in the memory 1.6 of the mobile sensor unit 1 and to subsequently send them to the central evaluation unit 3. This communication node 2*a* itself has no sensors. One again envisages the communication node 2*a* and the mobile sensor unit 1 being configured for the synchronisation of their clocks which has been described in the context of FIG. 4.

The communication node 2*a*, which is not a sensor node, can be provided for example in a foreman's office or in a changing room, where the gathering of measurement values of the second physical variable is not necessary. The mobile sensor units can then be stored or located in the environment of the communication node 2*a*. Each individual can then pick up their mobile sensor unit there before their work and bring it back there after their work, so that the data exchange can take place between the mobile sensor unit 1 and the communication node 2*a*.

FIG. 6 in the same representation as FIG. 3 shows a typical system which comprises a communication node 2*a* and several sensor nodes 2*b*, 2*c* which are each not designed as communication nodes. What are shown are two sensor nodes 2*b*, 2*c*, but there can also be more than two. Only the communication node 2*a* is configured for communication with the central evaluation unit 3, as is shown in the figure by a line. The mobile sensor units 1*a*-1*i* always communicate with the communication node 2*a* and the sensor nodes 2*b*, 2*c* when they are located in the environment. If the mobile sensor units 1 are in the environment of a sensor node 2*b*. 2*c*, then they receive the measurement values of the second physical variables which are gathered at the sensor nodes 2*b*, 2*c* and at the same time even gather measurement values of the first physical variables. All these measurement values are intermediately stored in a paired and time-resolved manner on the mobile sensor units 1, as described previously.

If the mobile sensor units 1 are then later brought into the environment of the communication node 2*a*, then the intermediately stored measurement values are forwarded to the communication node 2*a* and from there to the central evaluation unit 3. Herein, there can also be several communication nodes in the system. Some or all of these can simultaneously be sensor nodes.

LIST OF REFERENCE NUMERALS 1, 1*a-i* mobile sensor unit
1.1 sensor
1.1.1 movement sensor
1.2 transmitter or transmitting and receiving unit
1.2.1 Bluetooth antenna
1.3 energy store
1.3.1 battery
1.4 feedback device
1.5 clock
1.6 memory
1.4.1 feedback lamplet
1.4.2 feedback loudspeaker
1.4.3 feedback display
2 sensor and communication node
2*a* communication node
2*b-c* sensor node
2.1 receiver or transmitting and receiving unit
2.1.1 Bluetooth antenna
2.2 sensor
2.2.1 temperature sensor
2.2.2 brightness sensor
2.2.3 sound sensor
2.3 energy supply
2.3.1 mains plug
2.4 communication unit
2.4.1 mobile radio antenna
2.5 clock
2.6 memory
3 central evaluation unit
3.1 communication unit
3.1.1 mobile radio antenna
3.2 data bank
3.3 operator interface
3.4 cloud
4 individual
5.1 wearable designed as an armband
5.2 wearable designed as a glove
5.3 wearable designed as a piece of clothing
6 operator

The invention claimed is:

1. A system for monitoring a working situation, said system comprising:
at least one mobile sensor unit, configured to be carried by an individual;
at least one communication node;
at least one sensor node formed by the communication node or provided additionally; and
a central evaluation unit;
wherein the at least one mobile sensor unit comprises at least one sensor for measuring at least one first physical variable describing an activity or a state of the individual carrying the mobile sensor unit, wherein the system further comprises:
a transmitter for wireless transmission of measurement values of the at least one first physical variable detected by the at least one sensor of the mobile sensor unit, to the at least one communication node; and
an energy store to supply electricity to the transmitter, wherein the at least one sensor node comprises at least one sensor, different than the at least one sensor of the mobile sensor unit, for measuring at least one second physical variable describing a state of an environment of the sensor node;
wherein the at least one communication node comprises:
a receiver for receiving a measurement value of the at least one first physical variable transmitted by the transmitter of the mobile sensor unit; and
a communication unit for transmitting the measurement value of the at least one first physical variable received by the receiver of the communication node, and a measurement value of the at least one second physical variable, detected by the at least one sensor of the sensor node, to the central evaluation unit;
wherein the central evaluation unit comprises:
a communication unit for receiving the measurement value of the at least one first physical variable and the measurement value of the at least one second physical variable, said measurement values being transmitted by the communication unit of the communication node;
wherein the system is configured to assign the measurement value of the at least one second physical variable detected by the at least one sensor of the sensor node, to the mobile sensor unit located in the environment of the at least one sensor node, at least at one point in time and to transfer, store, and further process the assigned measurement value together with the measurement value of the at least one first physical variable detected by the at least one sensor of the mobile sensor unit located in the environment of the at least one sensor node, at least at the point in time, to the central evaluation unit as being assigned to one another, wherein the at least one second physical variable identifies a property of the environment, the property describing the state of the environment of the sensor node, and wherein a machine learning algorithm assigns a certain activity to the measurement value of the at least one first physical variable measured with the mobile sensor unit in the environment to identify a working process based on the measurement value of the at least one first physical variable measured with the mobile sensor unit in the environment, the assigned certain activity, and the property describing the state of the environment of the sensor node.

2. The system according to claim 1, wherein the at least one mobile sensor unit comprises a receiving unit and the at least one sensor node comprises a transmitting unit, in order to permit a bidirectional wireless communication between the at least one mobile sensor unit and the at least one sensor node and/or to permit a use of the sensor node as a radio beacon.

3. The system according to claim 2, wherein the at least one mobile sensor unit is configured to detect when it is located in the environment of a sensor node by way of a signal of the sensor node received by a receiving unit coupled to the at least one mobile sensor using, said sensor node acting as a radio beacon.

4. The system according to claim 3, wherein the at least one mobile sensor unit is configured to receive the measurement value of the at least one second physical variable detected by the at least one sensor of the at least one sensor node, with the receiving unit, when it is located in the environment of this sensor node, and using the transmitting unit to transmit the received measurement values of the at least one second physical variable together with the measurement value of the at least one first physical variable detected by the at least one sensor, to the receiver of the communication node when the communication node is in reach of its transmitter.

5. The system according to claim 4, wherein the at least one mobile sensor unit comprises a memory for intermediately storing the measurement value of the at least one second physical variable detected by the at least one sensor of the at least one sensor node and received by the receiving unit, and the measurement value of the at least one first physical variable detected by the at least one sensor, and/or is configured to temporally assign the measurement value of the at least one second physical variable detected by the at least one sensor of the at least one sensor node and are received by the receiving unit, to a time-dependent measurement value of the at least one first physical variable detected by the at least one sensor.

6. The system according to claim 5, wherein the mobile sensor unit and the communication node each comprise a clock and are configured to synchronize with the clock of one another.

7. The system according to claim 1, wherein the communication unit of the at least one communication node and the communication unit of the central evaluation unit are configured for bidirectional communication between the at least one communication node and the central evaluation unit.

8. The system according to claim 1, wherein the communication unit of the at least one communication node and the communication unit of the central evaluation unit are configured as wireless communication units, using at least one of, a mobile radio technology, a LAN, or a WLAN.

9. The system according to claim 1, wherein receiver of the at least one communication node is configured for locating the mobile sensor unit.

10. The system according to claim 9, wherein the at least one communication node and the central evaluation unit are configured to assign the measurement value of the at least one second physical variable detected by the at least one sensor of the sensor node, said sensor node being formed by the communication node, to the mobile sensor unit located in the environment of the communication node by the receiver of the communication node and to store them and/or further process them together with the measurement value of the at least one first physical variable detected by the at least one sensor of the mobile sensor unit, which is located in the environment of the communication node, as being assigned to one another.

11. The system according to claim 1, wherein the at least one sensor of the at least one mobile sensor unit is at least one of an acceleration sensor, a magnetometer, or a gyroscope or comprises at least one of an acceleration sensor, a magnetometer, a gyroscope.

12. The system according to claim 1, wherein the at least one sensor of the at least one sensor node is at least one of a temperature sensor or a brightness sensor or a vibration sensor or a sound sensor or comprises a temperature sensor, a brightness sensor, a vibration sensor, /or a sound sensor.

13. The system according to claim 1, wherein the at least one mobile sensor unit is configured to be wearable.

14. The system according to claim 1, wherein the at least one mobile sensor unit comprises a feedback device for sending information to the individual carrying the mobile sensor unit.

15. The system according to claim 14, wherein the feedback device is configured to send the information to the individual carrying the mobile sensor unit, as at least one of, an optical signal, a sound signal, via a display, or as a vibration.

16. The system according to claim 14, wherein the system is designed to output at least one of a warning or an instruction to the individual carrying the mobile sensor unit, by way of the feedback device based on the measurement value of the first physical variable and the second physical variable which are processed by the central evaluation unit.

17. The system according to claim 1, wherein the central evaluation unit comprises an operator interface.

18. The system according to claim 1, wherein the central evaluation unit is configured to evaluate the measurement value of the first physical variable and the second physical variable using at least one of machine learning or pattern recognition.

19. A method for monitoring a working situation using a system, said system comprising at least one mobile sensor unit configured to be carried by an individual, at least one communication node, at least one sensor node which is provided additionally to the communication node, and a central evaluation unit, the method comprising:
   measuring, using at least one sensor of the at least one mobile sensor unit, at least one first physical variable describing an activity or a state of an individual carrying the mobile sensor unit;

transmitting via wireless transmission, using a transmitter included in the at least one mobile sensor unit a measurement value of the at least one first physical variable to the at least one communication node;

supplying electricity to the transmitter from an energy store included in the at least one mobile sensor unit;

measuring at least one second physical variable describing a state of an environment of the at least one sensor node using at least one sensor of the at least one sensor node, the at least one sensor of the at least one sensor node being different than the at least one sensor of the mobile sensor unit;

receiving, at the mobile sensor unit a measured value of the at least one second physical variable detected by the at least one sensor of the at least one sensor node;

transmitting, using the mobile sensor unit, when the mobile sensor unit is located in the environment of the at least one sensor node, the received measurement value of the at least one second physical variable and the measurement value of the at least one first physical variable to the receiver of the communication node when the communication node is in reach of the transmitter, receiving, with a receiver coupled to the at least one communication node, the measurement value of the at least one first physical variable and the measurement value of the at least one second physical variable which are transmitted by the transmitter of the mobile sensor unit;

transmitting, using a communication unit coupled to the at least one communication node, the measurement value of the at least one first physical variable received by the receiver of the communication node, and measurement value of the at least one second physical variable detected by the at least one sensor of the sensor node, to the central evaluation unit;

receiving, at a communication unit coupled to the central evaluation unit the measurement value of the at least one first physical variable and the measurement value of the at least one second physical variable transmitted by the communication unit of the communication node;

assigning the measurement value of the at least one second physical variable detected by the at least one sensor of the at least one sensor node, to the mobile sensor unit located in the environment of the at least one sensor node, at least at one point in time, wherein the at least one second physical variable identifies a property of the environment, the property describing the state of the environment of the sensor node;

transferring the assigned measurement value and the measurement value of the at least one first physical variable detected by the at least one sensor of the mobile sensor unit located in the environment of the sensor node, at least at the point in time, to the central evaluation unit as being assigned to one another;

storing the transferred assigned measurement value and the transferred measurement value of the at least one first physical variable detected by the at least one sensor of the mobile sensor unit at the central evaluation unit;

arranging the at least one mobile sensor unit and the at least one communication node at one or more locations of at least one working site, wherein at least one of the at least one mobile sensor unit is carried by an individual or each by one of several individuals while moving about the working site;

assigning, with a machine learning algorithm, a certain activity to the stored transferred assigned measurement value of the at least one first physical variable detected by the at least one sensor of the mobile sensor unit in the environment; and identifying with the machine learning algorithm, based on the transferred measurement value of the at least one first physical variable measured with the mobile sensor unit in the environment, the assigned certain activity, and the property describing the state of the environment of the sensor node, a working process;

wherein, when the at least one mobile sensor unit is in the environment of the at least one sensor node, the at least one mobile sensor unit receives the measurement value of the second physical variable gathered at the sensor node and at the same time gathers the measurement value of the first physical variable, and intermediately stores the measurement value of the second physical variable gathered at the at least one sensor node and the gathered measurement value of the first physical variable in a paired and time-resolved manner and, when the at least one mobile sensor unit is brought into the environment of the communication node, the intermediately stored measurement values are forwarded to the communication node and then forwarded from the communication node to the central evaluation unit.

20. The method according to claim 19, wherein a feedback is given to the individual or at least one of the individuals in dependence on the measurement values of the at least one first and of the at least one second physical variable which are assigned to this individual, in order to improve ergonomics of the activities which are carried out by the individual or by the individuals, or to reduce physical and/or psychological burdens of the individual or of the individuals.

21. The method according to claim 19, wherein the measurement values of the at least one first physical variable are stored such that an assignment of these measurement values to the mobile sensor unit containing the at least one sensor with which they were detected, and/or to the individual carrying or having carried this mobile sensor unit, is no longer possible.

* * * * *